United States Patent
Perkins et al.

(10) Patent No.: US 9,523,786 B2
(45) Date of Patent: Dec. 20, 2016

(54) MONOLITHIC BAND-LIMITED INTEGRATED COMPUTATIONAL ELEMENTS

(71) Applicant: Halliburton Energy Services, Inc., Houston, TX (US)

(72) Inventors: David L. Perkins, The Woodlands, TX (US); Robert Paul Freese, Pittsboro, NC (US); Christopher Michael Jones, Houston, TX (US); Richard Neal Gardner, Raleigh, NC (US)

(73) Assignee: Halliburton Energy Services, Inc., Houston, TX (US)

( * ) Notice: Subject to any disclaimer, the term of this patent is extended or adjusted under 35 U.S.C. 154(b) by 37 days.

(21) Appl. No.: 14/425,107

(22) PCT Filed: Mar. 21, 2014

(86) PCT No.: PCT/US2014/031434
§ 371 (c)(1),
(2) Date: Mar. 2, 2015

(87) PCT Pub. No.: WO2015/142351
PCT Pub. Date: Sep. 24, 2015

(65) Prior Publication Data
US 2016/0231459 A1    Aug. 11, 2016

(51) Int. Cl.
*G01V 8/10* (2006.01)
*E21B 49/08* (2006.01)
(52) U.S. Cl.
CPC ............... *G01V 8/10* (2013.01); *E21B 49/081* (2013.01); *E21B 2049/085* (2013.01)

(58) Field of Classification Search
CPC ....................................................... G01V 8/10
See application file for complete search history.

(56) References Cited

U.S. PATENT DOCUMENTS

| | | |
|---|---|---|
| 4,659,178 A | 4/1987 | Kyogoku |
| 5,075,550 A | 12/1991 | Miller et al. |

(Continued)

FOREIGN PATENT DOCUMENTS

| | | | | |
|---|---|---|---|---|
| KR | 10-2011-0075539 A | * | 12/2009 | ............... G03F 7/00 |
| WO | WO 2004/015364 | | 2/2004 | |

(Continued)

OTHER PUBLICATIONS

KR 10-2011-0075539—LG Display Co. Ltd. English Translation obtained from kpsod.kipo.go.kr on May 26, 2016, pp. 1-16.*

(Continued)

*Primary Examiner* — David Porta
*Assistant Examiner* — Jeremy S Valentiner
(74) *Attorney, Agent, or Firm* — Benjamin Fite; Parker Justiss, P.C.

(57) ABSTRACT

An optical analysis tool includes an integrated computational element (ICE) including an ICE core to process light received by the ICE from a sample, when the tool is operated, such that the processed light is related, over a wavelength range, to a characteristic of the sample. Additionally, the ICE includes a filter monolithically coupled to the ICE core, the filter to block light at wavelengths that are either shorter than the wavelength range or longer than the wavelength range, or both, such that the ICE outputs, when the tool is operated, processed light that is passed by the filter.

24 Claims, 7 Drawing Sheets

(56) References Cited

U.S. PATENT DOCUMENTS

| | | | |
|---|---|---|---|
| 5,399,229 | A | 3/1995 | Stefani et al. |
| 5,453,716 | A | 9/1995 | Person et al. |
| 5,537,479 | A | 7/1996 | Kreisel et al. |
| 5,619,366 | A | 4/1997 | Rhoads et al. |
| 6,078,389 | A | 6/2000 | Zetter |
| 6,154,550 | A | 11/2000 | Beyer |
| 6,163,259 | A | 12/2000 | Barsumian et al. |
| 6,198,531 | B1* | 3/2001 | Myrick .................... G01J 3/28 356/213 |
| 6,213,250 | B1 | 4/2001 | Wisniewski et al. |
| 6,529,276 | B1 | 3/2003 | Myrick |
| 6,646,753 | B2 | 11/2003 | Zhang et al. |
| 6,804,060 | B1 | 10/2004 | Tsai et al. |
| 6,905,578 | B1 | 6/2005 | Moslehi et al. |
| 6,965,431 | B2 | 11/2005 | Vo-Dinh et al. |
| 7,138,156 | B1 | 11/2006 | Myrick et al. |
| 7,163,901 | B2 | 1/2007 | Downey |
| 7,332,044 | B2 | 2/2008 | Sidorin et al. |
| 7,679,563 | B2 | 3/2010 | Werner et al. |
| 7,697,141 | B2 | 4/2010 | Jones et al. |
| 7,753,847 | B2 | 7/2010 | Greenleaf et al. |
| 7,777,870 | B2 | 8/2010 | Hayes et al. |
| 7,792,644 | B2 | 9/2010 | Kotter et al. |
| 7,828,929 | B2 | 11/2010 | Lee et al. |
| 7,911,605 | B2 | 3/2011 | Myrick et al. |
| 7,920,258 | B2 | 4/2011 | Myrick et al. |
| 8,054,212 | B1 | 11/2011 | Holly et al. |
| 8,106,850 | B1 | 1/2012 | Gregoire et al. |
| 8,164,061 | B2 | 4/2012 | Pawlak et al. |
| 8,216,161 | B2 | 7/2012 | Darlington et al. |
| 8,252,112 | B2 | 8/2012 | Ovshinsky |
| 2004/0069942 | A1 | 4/2004 | Fujisawa et al. |
| 2005/0054928 | A1 | 3/2005 | Cerofolini |
| 2006/0029522 | A1 | 2/2006 | Theil |
| 2009/0182693 | A1 | 7/2009 | Fulton et al. |
| 2009/0219539 | A1 | 9/2009 | Myrick et al. |
| 2010/0245096 | A1* | 9/2010 | Jones .................... E21B 47/102 340/603 |
| 2011/0032398 | A1 | 2/2011 | Lenchenkov |
| 2011/0108721 | A1* | 5/2011 | Ford .................... E21B 47/102 250/269.1 |
| 2012/0211650 | A1* | 8/2012 | Jones .................... E21B 49/10 250/269.1 |
| 2012/0268744 | A1 | 10/2012 | Wolf et al. |
| 2013/0284894 | A1 | 10/2013 | Freese et al. |
| 2013/0284895 | A1 | 10/2013 | Freese et al. |
| 2013/0284896 | A1 | 10/2013 | Freese et al. |
| 2013/0284897 | A1 | 10/2013 | Freese et al. |
| 2013/0284898 | A1 | 10/2013 | Freese et al. |
| 2013/0284899 | A1 | 10/2013 | Freese et al. |
| 2013/0284900 | A1 | 10/2013 | Freese et al. |
| 2013/0284901 | A1 | 10/2013 | Freese et al. |
| 2013/0284904 | A1 | 10/2013 | Freese et al. |
| 2013/0286398 | A1 | 10/2013 | Freese et al. |
| 2013/0286399 | A1 | 10/2013 | Freese et al. |
| 2013/0287061 | A1 | 10/2013 | Freese et al. |

FOREIGN PATENT DOCUMENTS

| | | |
|---|---|---|
| WO | WO 2006/031733 | 3/2006 |
| WO | WO 2007/015115 | 2/2007 |
| WO | WO 2011/063086 | 5/2011 |
| WO | WO 2011/103066 | 8/2011 |
| WO | 2012/108885 | 8/2012 |
| WO | WO 2013/022556 | 2/2013 |

OTHER PUBLICATIONS

International Search Report and Written Opinion of the International Searching Authority issued in International Application No. PCT/US2014/031434 on Dec. 19, 2014; 12 pages.

Frey et al., "Temperature-dependent refractive index of silicon and germanium," NASA Goodard Space Flight Center, Greenbelt, MD, 2006, 10 pages.

Morton et al., "Optical Monitoring of Thin-films Using Spectroscopic Ellipsometry," Society of Vacuum Coaters, 45th Annual Technical Conference Proceedings, 2002, 7 pages.

Eastwood et al., "Filed applications of stand-off sensing using visible/NIR multivariate optical computing," Department of Chemistry and Biochemistry, University of South Carolina, SPE vol. 4199, 2001, 10 pages.

Paul et al., "Fabrication of mid-infrared frequency-selective surfaces by soft lithography", Applied Optics, v. 40, No. 25, Sep. 2001, 5 pages.

Haibach et al., "Precision in multivariate optical computing," Applied Optics, vol. 43, No. 10, Apr. 1, 2004, 11 pages.

J.A. Woollam Co., Inc., Characterizing Processes with EASE® In Situ Applications, Application Note, 2009, 3 pages.

Li, "Refractive Index of Silicon and Germanium and its Wavelength and Temperature Derivatives," Center for Information and Numerical Data Analysis and Synthesis, Purdue University, J. Phys. Chem. Ref. Data, vol. 9, No. 3, 1980, 98 pages.

Myrick, "Multivariate optical elements simplify spectroscopy," Laser Focus World, Mar. 1, 2002, access date Feb. 28, 2013, 3 pages http://www.laserfocusworld.com/articles/print/volume-38/issue-3/features/spectroscopy/multivariate-optical-elements-simplify-spectroscopy.html.

Myrick et al., "A single-element all-optical approach to chemometric prediction," Vibrational Spectroscopy 28, 2002, 9 pages.

Myrick et al., "Spectral tolerance determination for multivariate optical element design," Fresenius J Anal Chem, 369, 2001, 5 pages.

Myrick et al., "Application of multivariate optical computing to simple near-infrared point measurements," SPIE vol. 4574, Department of Chemistry and biochemistry, University of South Carolina, 2002, 8 pages.

Rabady et al., "High-resolution photometric optical monitoring for thin-film deposition," Applied Optics, Optical Society of America, vol. 43, No. 1, Jan. 1, 2004, 6 pages.

Priore et al., "Novel Imaging Systems: Multivariate Optical Computing in the UV-VIS," Department of Chemistry and Biochemistry, University of South Carolina, 2003, 5 pages.

Grader et al., "Fourier transform infrared spectroscopy of a single aerosol particle," J. Chem. Phys. 86 (11), Jun. 1, 1987, 7 pages.

Soyemi et al., "Novel Filter Design Algorithm for Multivariate Optical Computing," Advanced Environmental and Chemical Sensing Technology, SPIE vol. 4205, 2001, 12 pages.

Telemark, "Model 820 In-Situ Spectroscopic Optical Monitor," Dec. 2010, 4 pages.

Bossard et al., "The Design and fabrication of planar multiband metallodielectric frequency selective surfaces for infrared applications", IEEE Trans. on Antennas and Propagation, v. 50, No. 4, Apr. 2006, 12 pages.

Woollam et al., "Overview of Variable Angle Spectroscopic Ellipsometer (VASE), Part 1: Basic Theory and Typical Applications," Society of Photo-Optical Instrumentation Engineers, Critical Reviews of Optical Science Technology CR72, 1999, 28 pages.

Zoeller et al., "Substantial progress in optical monitoring by intermittent measurement technique," SPIE, Published in the processing of the OSD, Jena 2005, vol. 5963-13, 9 pages.

Extended European Search Report issued in European Application No. 14845017.4, dated Apr. 8, 2016.

\* cited by examiner

MONOLITHIC BAND-LIMITED INTEGRATED COMPUTATIONAL ELEMENTS

CLAIM OF PRIORITY

This application is a U.S. National Stage of International Application No. PCT/US2014/031434, filed Mar. 21, 2014.

BACKGROUND

The subject matter of this disclosure is generally related to optical analysis systems for analyzing a substance of interest, for example, crude petroleum, gas, water, or other wellbore fluids. For instance, the disclosed optical analysis systems use a band-limited integrated computational element (ICE) that includes an ICE core monolithically coupled to one or more band-limiting filters.

Information about a substance can be derived through the interaction of light with that substance. The interaction changes characteristics of the light, for instance the frequency (and corresponding wavelength), intensity, polarization, and/or direction (e.g., through scattering, absorption, reflection or refraction). Chemical, thermal, physical, mechanical, optical or various other characteristics of the substance can be determined based on the changes in the characteristics of the light interacting with the substance. As such, in certain applications, one or more characteristics of crude petroleum, gas, water, or other wellbore fluids can be derived in-situ, e.g., downhole at well sites, as a result of the interaction between these substances and light.

An ICE selectively weights, when operated as part of optical analysis tools, light modified by a sample in a particular wavelength range such that the weightings are related to one or more chemical or physical characteristics of the sample. The ICE includes an ICE core—which measures the various sample characteristics through the use of regression techniques—and one or more band-limiting filters—which limit the measured characteristics to the particular wavelength range. Because ICEs extract information from the light modified by a sample passively, they can be incorporated in low cost and rugged optical analysis tools. Hence, ICE-based downhole optical analysis tools can provide a relatively low cost, rugged and accurate system for monitoring quality of wellbore fluids, for instance.

DESCRIPTION OF DRAWINGS

Like reference symbols in the various drawings indicate like elements.

DETAILED DESCRIPTION

Figure 1:
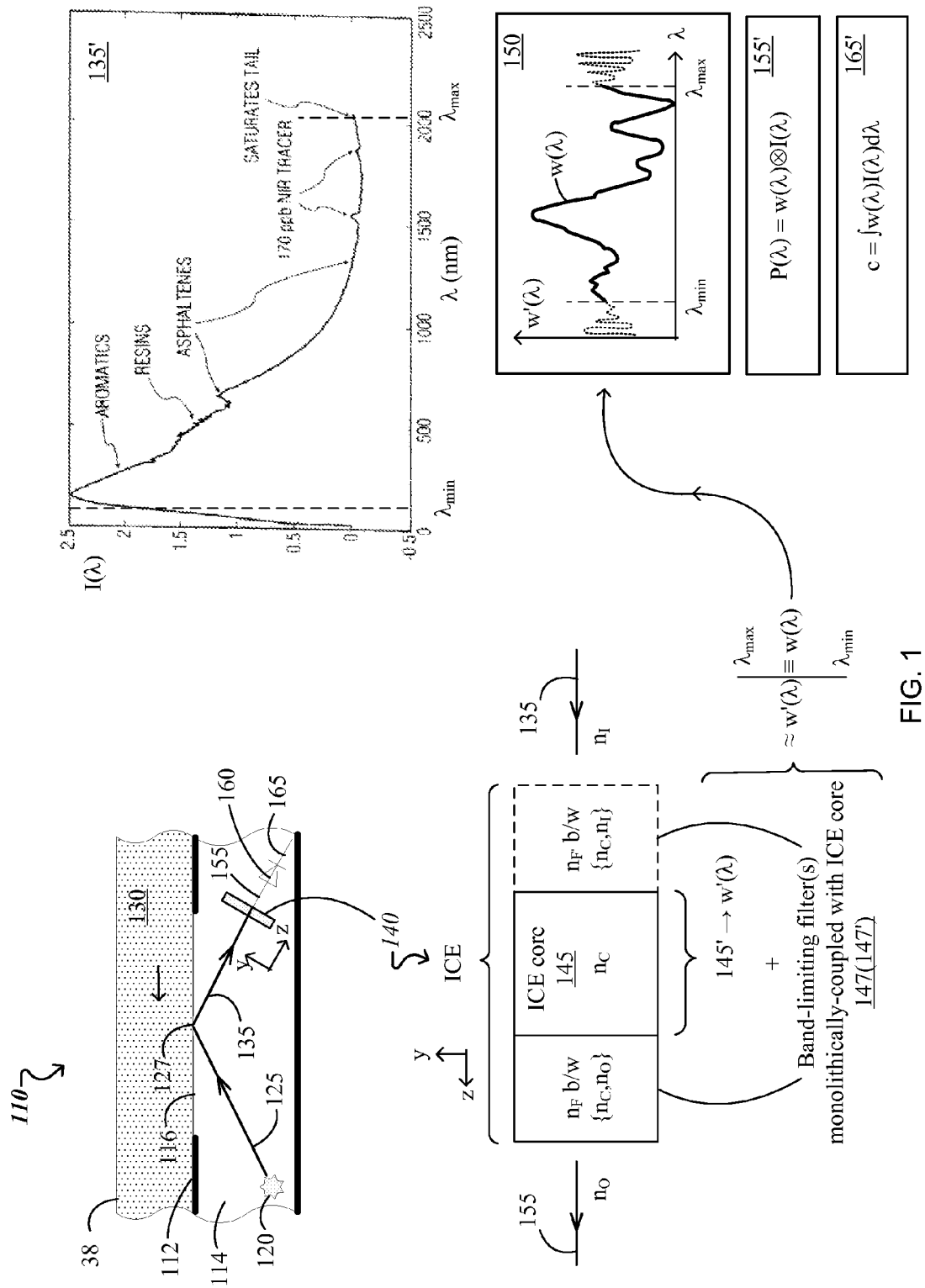
FIG. 1 shows an example of an optical analysis tool for measuring a property of a sample using a monolithic band-limited ICE.

In accordance with the disclosed technologies, optical analysis systems use a band-limited ICE that includes an ICE core monolithically coupled to one or more band-limiting filters. Here, the ICE core processes light received by the ICE from a sample, such that the processed light is related, over a wavelength range $[\lambda_{min},\lambda_{max}]$, to a characteristic of the sample. Additionally, a band-limiting filter that is monolithically coupled to the ICE core blocks light at wavelengths that are either shorter than $\lambda_{min}$ or longer than $\lambda_{max}$, or both. In this manner, the disclosed ICE outputs processed light that is passed by the band-limiting filter.

In some implementations, the ICE core of the band-limited ICE is an optical substrate with multiple stacked dielectric layers, each having a refractive index different from refractive indices of its adjacent layers. The specific number of layers, N, the optical properties of the layers, the optical properties of the substrate, and the physical thickness of each of the layers that compose the ICE core are selected so that the light processed by the ICE core is related to one or more characteristics of the sample. In other implementations, the ICE core of the band-limited ICE contains liquid crystals, liquids and/or gases that are selected so that the light processed by the ICE core is related to one or more characteristics of the sample. Here, the ICE core may contain a vessel which houses the gases, liquids or liquid crystals. In some other implementations, the ICE core of the band-limited ICE includes acousto-optic elements, holographic elements, gratings, micro-electro-mechanical systems (MEMS) based devices or frequency selective surfaces, for example, that output transmitted, reflected, and/or absorbed light that is related to one or more characteristics of the sample.

The wavelength range $[\lambda_{min},\lambda_{max}]$ over which the light processed by the ICE core relates to the characteristic of the sample represents an operational optical bandwidth of the ICE, in analogy with an operational electronic bandwidth of an electronic computational device. In general, a specified operational optical bandwidth of an ICE can be accomplished by placing a band-pass optical filter (or combination of long-pass and short-pass optical filters to achieve an overall band-pass optical filter) in an optical path that includes (i) the sample, (ii) the ICE core that processes the light received from the sample and (iii) an optical transducer (e.g., a detector) that detects the light processed by the ICE core and outputs a signal that is related to one or more characteristics of the sample. Conventionally, a band-limiting filter is spaced apart from the ICE core. In contrast, the band-limiting filter is monolithically coupled to the ICE core in accordance with the disclosed technologies. In this manner, the disclosed ICE having a monolithically coupled ICE core and band-limiting filter—referred herein as a monolithic band-limited ICE—is more compact and requires reduced optical alignment complexity relative to conventional band-limited ICEs having the ICE core spaced apart from the band-limiting filter. In this manner, optical analysis systems based on monolithic band-limited ICEs can be advantageously fabricated to be more compact and rugged than optical analysis systems based on conventional band-limited ICEs. Additionally, an ICE for which the ICE core is monolithically coupled to the band-limiting filter(s) contains one less optical interface, for each of the band-limiting filters, relative to a conventional band-limited ICE for which the ICE core is spaced apart from the band-limiting filter(s). Hence, signal-to-noise ratios (SNR) of the monolithic band-limited ICEs can advantageously be larger than the SNR of conventional band-limited ICEs.

In some implementations of the disclosed ICE having a monolithically coupled ICE core and band-limiting filter, a value of an effective refractive index $n_F$ associated with the band-limiting filter is chosen to be between a value of an effective refractive index $n_C$ associated with the ICE core and a value of a refractive index $n_O$ of an output medium. As such, $|n_C-n_F|<|n_O-n_C|$ and $|n_F-n_O|<|n_O-n_C|$. For example, when an optical transducer is spaced apart from the disclosed ICE, the output medium is the ambient between the monolithic band-limited ICE and the optical transducer. As another example, when an optical transducer is monolithically coupled to the disclosed ICE, the output medium is a constituent material of the optical transducer. In this manner, the band-limiting filter that is monolithically coupled to the ICE core of the disclosed ICE advantageously reduces a refractive index mismatch $|n_O-n_C|$ between the ICE core of a conventional band-limited ICE and the output medium. Examples of the effective refractive index $n_C$ associated with the ICE core along with examples of the effective refractive index $n_F$ associated with the monolithically coupled band-limiting filter are described below in connection with FIGS. 2A-2C, 3 and 4 for various combinations of different types of ICE cores and different types of band-limiting filters.

In some implementations of the disclosed ICE having a monolithically coupled ICE core and band-limiting filter, a value of an effective refractive index $n_F$ associated with the band-limiting filter is chosen to be between a value of an effective refractive index $n_C$ associated with the ICE core and a value of a refractive index $n_I$ of an input medium. As such, $|n_I-n_F|<|n_I-n_C|$ and $|n_F-n_C|<|n_I-n_C|$. For example, when the disclosed ICE is spaced apart from a sample, the input medium is the ambient between the sample and the monolithic band-limited ICE. As another example, when a sample is monolithically coupled to the disclosed ICE, the input medium is a constituent material of the sample. In this manner, the band-limiting filter that is monolithically coupled to the ICE core of the disclosed ICE advantageously reduces a refractive index mismatch $|n_I-n_C|$ between the ICE core of a conventional band-limited ICE and the input medium.

Prior to describing example implementations of monolithic band-limited ICEs, optical analysis tools based on the disclosed ICEs are described below along with examples of their use in oil/gas exploration.

FIG. 1 shows an example of an optical analysis tool 110 for measuring a property of a sample 130 using a monolithic band-limited ICE 140. In this example, the optical analysis tool 110 includes a light source 120, the monolithic band-limited ICE 140 and an optical transducer 160. The optical analysis tool 110 has a frame 112 such that the foregoing components are arranged in an enclosure 114 thereof. A cross-section of the optical analysis tool 110 in a plane perpendicular to the page can vary, depending on the space available. For example, the optical analysis tool's cross-section can be circular or rectangular, for instance. The optical analysis tool 110 directs light to a sample 130 through an optical interface 116, e.g., a window in the frame 112. The optical analysis tool 110 is configured to probe the sample 130 (e.g., wellbore fluids stationary or flowing) in a wellbore 38 through the optical interface 116 and to determine an amount (e.g., a value) of a given characteristic (also referred to as a property to be measured) of the probed sample 130. The property to be measured can be any one of multiple properties of the sample 130 including concentration of a given substance in the sample, a gas-oil-ratio (GOR), pH value, density, viscosity, etc.

The light source 120 outputs light with a source spectrum over a particular wavelength range. In some implementations, the source spectrum can have non-zero intensity over the entire or most of the particular wavelength range. In some implementations, the source spectrum extends through UV-vis (0.2-0.8 µm) and near-IR (0.8-2.5 µm) spectral ranges. Alternatively, or additionally, the source spectrum extends through an IR (2.5-100 µm) spectral range. In some implementations, the light source 120 is tunable and is configured in combination with time resolved signal detection and processing.

The light source 120 is arranged to direct a probe beam 125 of the source light towards the optical interface 116 where it illuminates the sample 130 at a location 127. The source light in the probe beam 125 interacts with the sample 130 and reflects off it as light modified by the sample 130. The light modified by the sample 135 has a modified spectrum $I(\lambda)$ 135' over the particular wavelength range. In general, the modified spectrum $I(\lambda)$ 135' encodes information about multiple characteristics associated with the sample 130, and more specifically the encoded information relates to current values of the multiple characteristics. In the example illustrated in FIG. 1, the modified spectrum 135' contains information about one or more characteristics of the sample 130.

With continued reference to FIG. 1, and the Cartesian coordinate system provided therein for reference, the monolithic band-limited ICE 140 is arranged to receive a beam 135 of the sample modified light, and is configured to process it and to output a beam 155 of processed light. The beam 135 of sample modified light is incident along the z-axis on an input optical interface of the monolithic band-limited ICE 140, and the beam 155 of processed light is output along the z-axis—after transmission through the monolithic band-limited ICE 140—at an output interface thereof. In the example illustrated in FIG. 1, the monolithic band-limited ICE 140 includes an ICE core 145 monolithically coupled to one or more band-limiting filters 147, 147'. The ICE core 145 processes the sample modified light 135 by weighting it in accordance with an optical spectrum $w(\lambda)$ 150 associated, over a wavelength range $[\lambda_{min}, \lambda_{max}]$, with a characteristic to be measured. The filter 147 or the combination of filters 147, 147' blocks light shorter than $\lambda_{min}$ and longer than $\lambda_{max}$, such that processed light 155 output by the monolithic band-limited ICE 140 is limited to the wavelength range $[\lambda_{min}, \lambda_{max}]$ over which the optical spectrum $w(\lambda)$ 150 is associated with the characteristic to be measured.

The optical spectrum $w(\lambda)$ 150 is determined offline by applying conventional processes to a set of calibration spectra $I(\lambda)$ of the sample 130 which correspond to respective known values of the characteristic to be measured. As illustrated by optical spectrum $w(\lambda)$ 150, optical spectra generally may include multiple local maxima (peaks) and minima (valleys) between $\lambda_{min}$ and $\lambda_{max}$. The peaks and valleys may have the same or different amplitudes. For instance, an optical spectrum $w(\lambda)$ can be determined through regression analysis of $N_c$ calibration spectra $I_j(\lambda)$ of a sample 130, where $j=1, \ldots, N_c$, such that each of the calibration spectra $I_j(\lambda)$ corresponds to an associated known value of a given characteristic for the sample. A typical number $N_c$ of calibration spectra $I_j(\lambda)$ used to determine the optical spectrum $w(\lambda)$ 150 through such regression analysis can be $N_c=10$, 40 or 100, for instance. The regression analysis outputs, within the $N_c$ calibration spectra $I_j(\lambda)$, a spectral pattern that is unique to the given characteristic. The spectral pattern output by the regression analysis corresponds to the optical spectrum $w(\lambda)$ 150. In this manner, when a value of the given characteristic for the sample 130 is unknown, a modified spectrum $I_u(\lambda)$ of the sample 130 is acquired by interacting the probe beam 125 with the sample 130, then the modified spectrum $I_u(L)$ is weighted by the ICE core 145 of the monolithic band-limited ICE 140 to determine a magnitude of the spectral pattern corresponding to the optical spectrum $w(\lambda)$ 150 within the modified spectrum $I_u(\lambda)$. The determined magnitude is proportional to the unknown value of the given characteristic for the sample 130.

For example, the sample 130 can be a mixture (e.g., the wellbore fluid in a wellbore 38) containing substances X, Y and Z, and the characteristic to be measured for the mixture is concentration $c_X$ of substance X in the mixture. In this case, $N_c$ calibration spectra $I_j(\lambda)$ were acquired for $I_j(\lambda)$, samples of the mixture having respectively known concentration values for each of the substances contained in the $N_c$ samples. By applying regression analysis to the $N_c$ calibration spectra $I_j(\lambda)$, a first spectral pattern that is unique to the concentration $c_X$ of the X substance can be detected (recognized), such that the first spectral pattern corresponds to a first optical spectrum $w_{cX}(\lambda)$ associated with a first ICE core, for example. Similarly, second and third spectral patterns that are respectively unique to concentrations $c_Y$ and $c_Z$ of the Y and Z substances can also be detected, such that the second and third spectral patterns respectively correspond to second and third optical spectra $w_{cY}(\lambda)$ and $w_{cZ}(\lambda)$ respectively associated with second and third ICE cores. In this manner, when a new sample of the mixture (e.g., the wellbore fluid in a wellbore 38) has an unknown concentration $c_X$ of the X substance, for instance, a modified spectrum $I_u(\lambda)$ of the new sample can be acquired by interacting the probe beam with the mixture, then the modified spectrum $I_u(\lambda)$ is weighted with the first ICE core to determine a magnitude of the first spectral pattern within the modified spectrum $I_u(\lambda)$. The determined magnitude is proportional to the unknown value of the concentration $c_X$ of the X substance for the new sample.

In some implementations described in detail below in connection with FIGS. 2A-2C, the ICE core 145—includes N layers of materials stacked on a substrate, such that refractive indices of adjacent layers are different from each other. A set of ICE core design parameters 145' of the ICE core 145—which here includes the total number N of stacked layers, the refractive indices of adjacent stacked layers, and the thicknesses of the N stacked layers—corresponds to an optical spectrum $w'(\lambda)$ associated with this embodiment of the ICE core 145. In other implementations described in detail below in connection with FIG. 3, the ICE core 145 includes a layer of conductive material patterned as laterally-displaced periodic structures over a dielectric substrate, such that the patterned layer forms a frequency-selective surface (FSS). A set of ICE core design parameters 145' of the ICE core 145—which here includes one or more of dimensions of lateral features of the FSS pattern, materials and thicknesses of the substrate and patterned layer, and one or more arrangements of the lateral features of the FSS pattern, e.g., triangular, rectangular, hexagonal or circular—corresponds to an optical spectrum $w'(\lambda)$ associated with this embodiment of the ICE core 145. In some other implementations described in detail below in connection with FIG. 4, the ICE core 145 includes N spectral filters that are supported by a substrate and laterally-distributed relative to an input optical interface of the ICE core 145. A set of ICE core design parameters 145' of the ICE core 145—which here includes the total number N of spectral filters and their relative areas—corresponds to an optical spectrum $w'(\lambda)$ associated with this embodiment of the ICE core 145.

In either of the foregoing ICE core embodiments (or other ICE core embodiments disclosed below in this specification), the set of ICE core design parameters 145' is chosen such that the optical spectrum $w'(\lambda)$ associated with the ICE core 145 is spectrally equivalent, over the wavelength range $[\lambda_{min}, \lambda_{max}]$, to an optical spectrum $w(\lambda)$ 150 associated with the characteristic to be measured. Contributions of the optical spectrum $w'(\lambda)$ associated with the ICE core 145 that are from wavelengths outside the wavelength range $[\lambda_{min}, \lambda_{max}]$ are removed from the processed light 155, by the one or more band-limiting filters 147, 147' monolithically coupled to the ICE core 145, to reduce analysis noise potentially caused by such "outside-of-band" contributions which may not be spectrally equivalent to the optical spectrum $w(\lambda)$ 150 associated with the characteristic to be measured. In this manner, contributions of the optical spectrum $I(\lambda)$ 135' of the sample modified light that are from wavelengths outside the wavelength range $[\lambda_{min}, \lambda_{max}]$ are weighted to zero.

In addition to limiting the processed light 155 to the wavelength range $[\lambda_{min}, \lambda_{max}]$ over which the optical spectrum $w(\lambda)$ 150 is associated with the characteristic to be measured, the band-limiting filters 147, 147' monolithically coupled to the ICE core 145 can reduce a mismatch $|n_C - n_O|$ between an effective refractive index $n_C$ associated with the ICE core 145 and a refractive index $n_O$ of an output medium, or a mismatch $|n_I - n_C|$ between a refractive index $n_I$ of an input medium and the effective refractive index $n_C$ associated with the ICE core 145. Examples of the effective refractive index $n_C$ associated with an ICE core are described below in connection with FIGS. 2A-2C, 3 and 4 for different types of ICE cores.

For example, when the optical transducer 160 is spaced apart from the monolithic band-limited ICE 140, the output medium is the ambient between the monolithic band-limited ICE 140 and optical transducer 160. As another example, when the optical transducer 160 is monolithically coupled to the monolithic band-limited ICE 140, the output medium is a constituent material of the optical transducer 160. Here, a value of the effective refractive index $n_F$ associated with the band-limiting filter 147 is chosen to be between a value of the effective refractive index $n_C$ associated with the ICE core 145 and a value of the refractive index $n_O$ of the output medium. As such, $|n_C - n_F| < |n_O - n_C|$ and $|n_F - n_O| < |n_O - n_C|$. In this manner, the band-limiting filter 147 that is monolithically coupled to the ICE core 145 of the monolithic band-limited ICE 140 advantageously reduces a refractive index mismatch $|n_O - n_C|$ between the ICE core 145 and the output medium. In some implementations, the band-limiting filter 147 can be formed from constitutive materials mixed in a matrix. In this case, the effective refractive index $n_F$ associated with the band-limiting filter 147 is a weighted average of individual refractive indices of the constitutive materials. In other implementations, the band-limiting filter 147 can be formed as a stack of layers, e.g., as interference filters. In this case, the effective refractive index $n_F$ associated with the band-limiting filter 147 is a particular function of individual refractive indices of the constitutive layer materials as described in literature, e.g., for all-dielectric interference (ADI) filters. (See e.g., B. Dorband et. al, in Metrology of Optical Components and systems, at pages 354-357, as part of vol. 5 of the Handbook of Optical Systems, edited by H. Gross and published in 2012.)

Further, in some cases when the monolithic band-limited ICE 140 is spaced apart from the sample 130, the input medium is the ambient between the sample 130 and the monolithic band-limited ICE 140. In other cases when the monolithic band-limited ICE 140 is monolithically coupled to the sample 130, the input medium is a constituent material of the sample 130. Here, a value of the effective refractive index $n_F$ associated with the band-limiting filter 147' is chosen to be between a value of the refractive index $n_I$ of the input medium and the value of the effective refractive index $n_C$ associated with the ICE core 145. As such, $|n_I-n_F|<|n_I-n_C|$ and $|n_C-n_F|<|n_I-n_C|$. In this manner, the band-limiting filter 147' that is monolithically coupled to the ICE core 145 of the monolithic band-limited ICE 140 advantageously reduces a refractive index mismatch $|n_I-n_C|$ between the input medium and the ICE core 145.

Continuing the description of functional aspects of the optical analysis tool 110, the beam 155 of processed light output by the monolithic band-limited ICE 140 has a processed spectrum $P(\lambda)=w(\lambda)\otimes I(\lambda)$ 155' over the wavelength range $[\lambda_{min},\lambda_{max}]$ such that the processed spectrum 155' represents the modified spectrum $I(\lambda)$ 135' weighted by the optical spectrum $w(\lambda)$ 150 associated with the characteristic to be measured.

The beam 155 of processed light is directed from the monolithic band-limited ICE 140 to the optical transducer 160, which detects the processed light 155 and outputs a detector signal 165. A value (e.g., a voltage) of the detector signal 165 is a result of an integration of the processed spectrum 155' over the wavelength range $[\lambda_{min},\lambda_{max}]$ and is related to the unknown value "c" 165' of the characteristic to be measured for the sample 130.

In some implementations, the optical analysis tool 110 can include a second monolithic band-limited ICE (not shown in FIG. 1) associated with a second optical spectrum $w''(\lambda)$. Here, a second set of ICE core design parameters 145'' is chosen such that the second optical spectrum $w''(\lambda)$ is associated, over the wavelength range $[\lambda_{min},\lambda_{max}]$ with a second characteristic of the sample 130. Hence, a second processed spectrum represents the modified spectrum $I(\lambda)$ 135' weighted by the second optical spectrum $w''(\lambda)$ over the wavelength range $[\lambda_{min},\lambda_{max}]$, such that a second value of a second detector signal is related to a value of the second characteristic for the sample 130.

In some implementations, the value 165' of the characteristic to be measured can be logged along with a measurement time, geo-location, and other metadata, for instance. In some implementations, the detector signal 165, which is related to a characteristic to be measured by the optical analysis tool 110, can be used as a feedback signal to adjust the characteristic of the sample, to modify the sample or environmental conditions associated with the sample, as desired.

In the example illustrated in FIG. 1, the monolithic band-limited ICE 140 of the optical analysis tool 110 is described generally as an ICE core 145 monolithically coupled to one or more band-limited filters 147, 147'. Example implementations of the monolithic band-limited ICE 140 are described below.

Figure 2A:
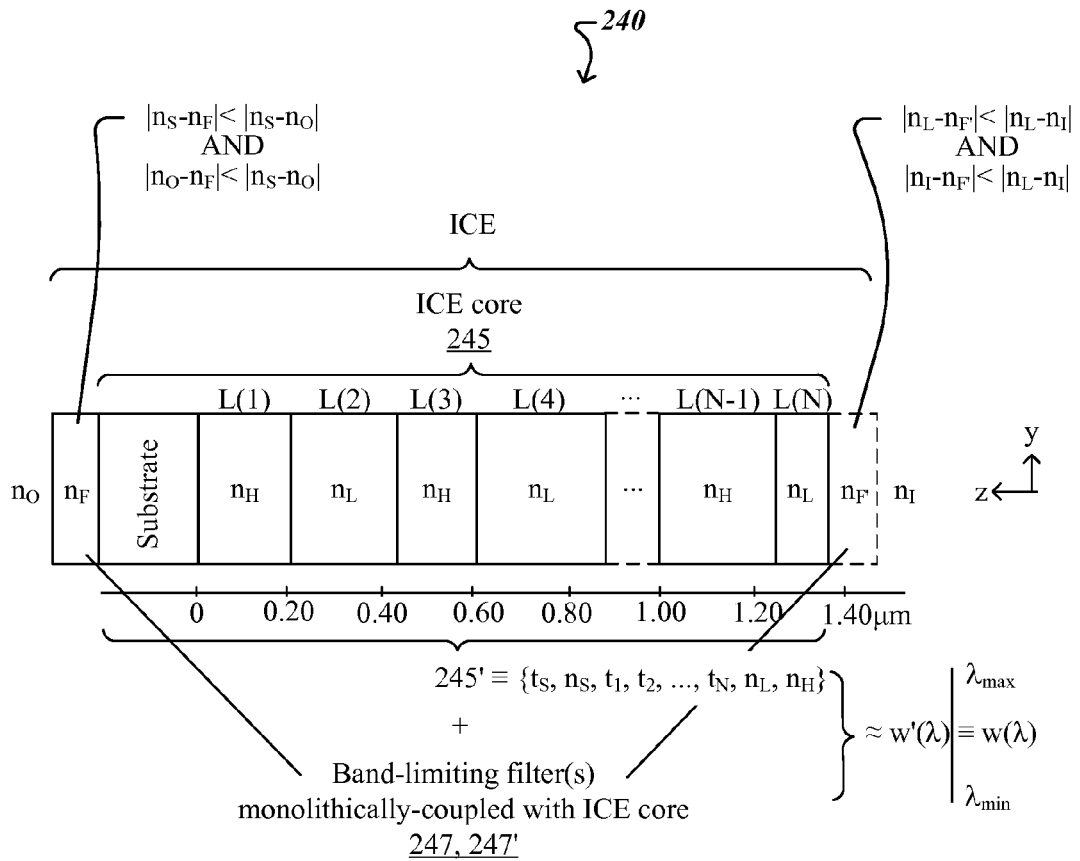
FIGS. 2A-2C show aspects of a monolithic band-limited ICE with an ICE core that includes dielectric layers stacked on a substrate.
Figure 2B:
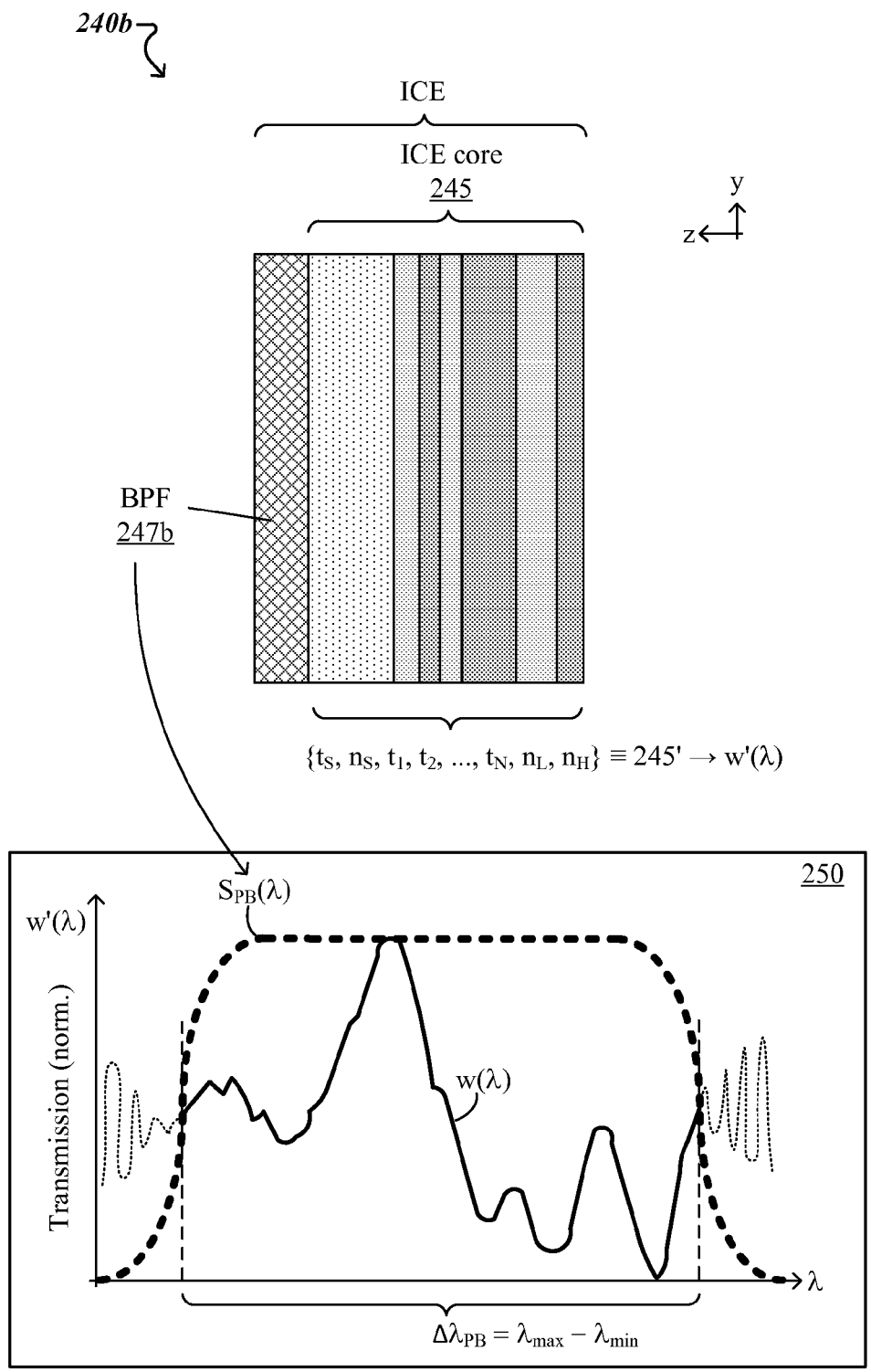
Figure 2C:
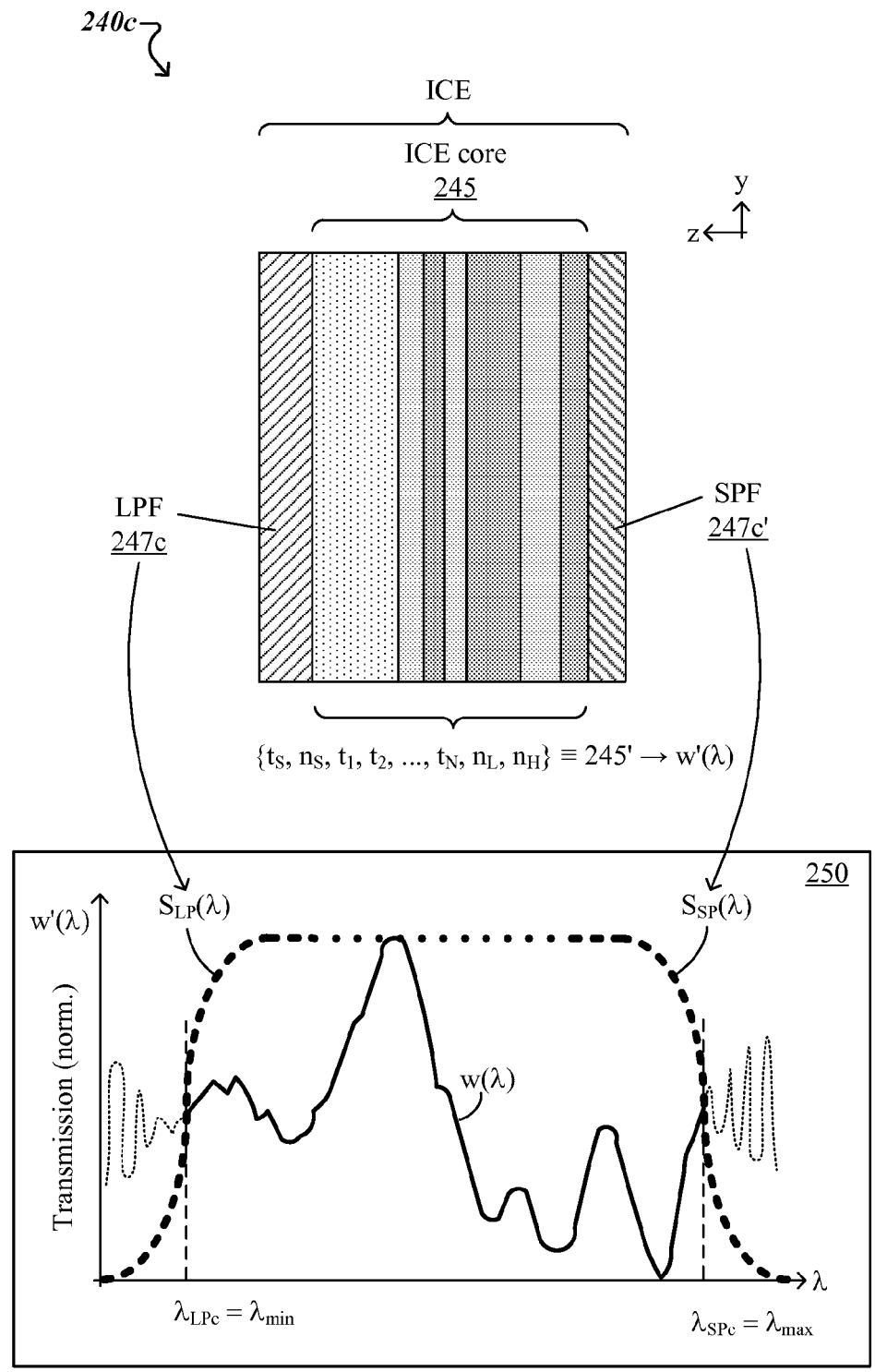

FIGS. 2A-2C show aspects of a monolithic band-limited ICE 240 with an ICE core 245 that includes dielectric layers stacked on a substrate. Here, the monolithic band-limited ICE 240 further includes one or more band-limiting filters 247, 247' that are monolithically coupled to the ICE core 245. The monolithic band-limited ICE 240 represents an embodiment of the monolithic band-limited ICE 140 of the optical analysis tool 110 described above in connection with FIG. 1.

In this example, the ICE core 245 includes N layers of materials stacked on the substrate, such that refractive indices of constitutive materials of adjacent layers are different from each other. The total number of stacked layers can be between 2 and 50, for instance. Throughout this specification, the refractive index "n" of a layer material has a complex value, $Re(n)+iIm(n)$. $Re(n)$ represents a real component of the complex index of refraction responsible for refractive properties of the material, and $Im(n)$ represents an imaginary component of the complex index of refraction (also known as extinction coefficient K) responsible for absorptive properties of the material.

The substrate material can be BK7, diamond, Ge, ZnSe (or other optical transparent dielectric material), and can have a thickness in the range of 0.02-2 mm, for instance, to insure structural integrity of the ICE core 245. An index of refraction of the substrate is $n_S$. Materials of adjacent layers of the ICE core 245 are selected to have a first index of refraction $n_H$ (e.g., Si), and a second index of refraction $n_L$ (e.g., $SiO_2$). Here, $n_{Si}\approx2.4>n_{SiO2}\approx1.5$. For other material pairings, however, the difference between the first refractive index $n_H$ and second refractive index $n_L$ may be much smaller, e.g., $n_H\approx1.6>n_L\approx1.5$. The use of two materials for fabricating the N layers is chosen for illustrative purposes only. For example, a plurality of materials having different indices of refraction, respectively, can be used.

A set of ICE core design parameters 245'—which includes the total number of stacked layers N; the refractive indices $n_H$, $n_L$ of adjacent stacked layers and the refractive index $n_S$ of the substrate; and the thicknesses of the N stacked layers $t_1, t_2, \ldots, t_N$—of the ICE core 145 corresponds to an optical spectrum $w'(\lambda)$ associated with the ICE core 245. The set of ICE core design parameters 245' is chosen such that the optical spectrum $w'(\lambda)$ associated with the ICE core 245 is spectrally equivalent, over the wavelength range $[\lambda_{min}, \lambda_{max}]$, to an optical spectrum $w(\lambda)$ 250 associated with a characteristic of a sample to be measured. Contributions of the optical spectrum $w'(\lambda)$ associated with the ICE core 245 that are from wavelengths outside the wavelength range $[\lambda_{min}, \lambda_{max}]$ are removed from the processed light by the one or more band-limiting filters 247, 247' monolithically coupled to the ICE core 245, to reduce analysis noise potentially caused by such "outside-of-band" contributions which may not be spectrally equivalent to the optical spectrum $w(\lambda)$ 250 associated with the characteristic to be measured.

In some implementations, the band-limiting filter 247 is integrally formed on a surface of the substrate of the ICE core 245 opposing a surface of the substrate on which the N layers are stacked. Also, the band-limiting filter 247' is integrally formed on a distal-most surface of the stacked layers relative to the substrate. In the example illustrated FIG. 2A, the band-limiting filter 247' is stacked on the last layer $L_N$ of the stack of layers of the ICE core 245. In other implementations, the stack of layers $L_1, L_2, \ldots, L_N$ of the ICE core 245 can be formed on a substrate that includes (is pre-formed with) a band-pass filter 247, for instance. In either of these implementations, the band-limiting filters 247, 247' can be formed from one or more constitutive materials. For example, the constitutive materials of the band-limiting filters 247, 247' can be mixed in a matrix. In this case, an effective refractive index $n_F$ (or $n_F'$) associated with the band-limiting filter 247 (or 247') is a weighted average of individual refractive indices of the constitutive materials. As another example, the constitutive materials of the band-limiting filters 247, 247' can be formed as a stack of layers, e.g., as interference filters. In this case, the effective refractive index $n_F$ (or $n_F'$) associated with the band-limiting filter 247 (or 247') is a particular function of individual refractive indices of the constitutive layer materials as described in literature, e.g., for ADI filters.

FIG. 2B shows an implementation of the monolithic band-limited ICE 240b which includes (i) the ICE core 245 with the dielectric layers stacked on a first surface of the substrate and (ii) a band-pass filter 247b integrally-formed on a second surface of the substrate opposing the first surface. In an alternative implementation, not shown in FIG. 2B, a band-pass filter 247b' is integrally-formed on the last layer $L_N$ of the stacked dielectric layers of the ICE core 245.

A pass-band envelope $S_{PB}(\lambda)$ of the band-pass filter 247b (represented in the graph of FIG. 2B as a dashed-curve) is overlaid on the optical spectrum $w'(\lambda)$ associated with the ICE core 245. A pass-band $\Delta\lambda_{PB} = \lambda_{max} - \lambda_{min}$ of the band-pass filter 247b is chosen to coincide with a portion (represented as a solid curve) of the optical spectrum $w'(\lambda)$ associated with the ICE core 245 that is spectrally equivalent to the optical spectrum $w(\lambda)$ 250 associated with the characteristic to be measured. In this manner, portions (represented as dotted curves) outside of the wavelength range $[\lambda_{min}, \lambda_{max}]$ of the optical spectrum $w'(\lambda)$ associated with the ICE core 245 are blocked by the integrally-formed band-pass filter 247b.

In some cases, when the band-pass filter 247b is integrally-formed on the substrate as shown in FIG. 2B, a constituent material of the band-pass filter 247b is chosen such that each of (i) the mismatch of refractive index $|n_S - n_{BPF}|$ for the processed light 155 across the optical interface between the substrate and the band-pass filter 247b and (ii) a mismatch of refractive index $|n_{BPF} - n_O|$ for the processed light 155 across an output optical interface between the band-pass filter 247b and the output medium downstream from the monolithic band-limited ICE 240b is smaller than the mismatch of refractive index $|n_S - n_O|$ for the processed light 155 if the output optical interface were between the substrate and the output medium. In alternative cases, when a band-pass filter 247b' is integrally-formed on the last layer $L_N$ of the stacked dielectric layers of the ICE core 245 (not shown in FIG. 2B), a constituent material of the band-pass filter 247b' is chosen such that each of (i) the mismatch of refractive index $|n_I - n_{BPF}|$ for the sample modified light 135 across an input optical interface between the band-pass filter 247b' and the input medium upstream from the monolithic band-limited ICE 240b and (ii) a mismatch of refractive index $|n_{BPF} - n_{LN}|$ for the filtered light across an optical interface between the band-pass filter 247b' and the last layer $L_N$ of the ICE core 245 is smaller than the mismatch of refractive index $|n_I - n_{LN}|$ for the sample modified light 135 if the input optical interface were between the input medium and the last layer $L_N$ of the ICE core 245.

FIG. 2C shows an implementation of the monolithic band-limited ICE 240c which includes (i) the ICE core 245 with the dielectric layers stacked on a first surface of the substrate, (ii) a long-pass filter 247c integrally-formed on a second surface of the substrate opposing the first surface, and (iii) a short-pass filter 247c' integrally-formed on the last layer $L_N$ of the stacked dielectric layers of the ICE core 245. In an alternative implementation, not shown in FIG. 2C, the integrally-formed filter 247c is a short-pass filter and the integrally-formed filter 247c' is a long-pass filter.

A long-pass envelope $S_{LP}(\lambda)$ of the long-pass filter 247c and a short-pass envelope $S_{SP}(\lambda)$ of the short-pass filter 247c' (each represented in the graph of FIG. 2C as a dashed-curve) are overlaid on the optical spectrum $w'(\lambda)$ associated with the ICE core 245. A long-pass cut-off wavelength $\lambda_{LPc}$ of the long-pass filter 247c is chosen to coincide with $\lambda_{min}$, $\lambda_{LPc} \approx \lambda_{min}$, such that the long-pass filter 247c blocks light with wavelengths shorter than $\lambda_{min}$, and a short-pass cut-off wavelength $\lambda_{SPc}$ of the short-pass filter 247c' is chosen to coincide with $\lambda_{max}$, $\lambda_{SPc} \approx \lambda_{max}$, such that the short-pass filter 247c' blocks light with wavelengths longer than $\lambda_{max}$. In this manner, the combination of integrally-formed long-pass filter 247c and short-pass filter 247c' generate a pass-band between $\lambda_{min}$ and $\lambda_{max}$ that coincides with a portion (represented as a solid curve) of the optical spectrum $w'(\lambda)$ associated with the ICE core 245 that is spectrally equivalent to the optical spectrum $w(\lambda)$ 250 associated with the characteristic to be measured. In this manner, portions (represented as dotted curves) outside of the wavelength range $[\lambda_{min}, \lambda_{max}]$ of the optical spectrum $w'(\lambda)$ associated with the ICE core 245 are blocked by the combination of integrally-formed long-pass filter 247c and short-pass filter 247c'.

In some cases, when the long-pass filter 247c is integrally-formed on the substrate and the short-pass filter 247c' is integrally-formed on the last layer $L_N$ of the stacked dielectric layers of the ICE core 245 as shown in FIG. 2C, a constituent material of the long-pass filter 247c is chosen such that each of (i) the mismatch of refractive index $|n_S - n_{LPF}|$ for the processed light 155 across the optical interface between the substrate and the long-pass filter 247c and (ii) a mismatch of refractive index $|n_{LPF} - n_O|$ for the processed light 155 across an output optical interface between the long-pass filter 247c and the output medium downstream from the monolithic band-limited ICE 240c is smaller than the mismatch of refractive index $|n_S - n_O|$ for the processed light 155 if the output optical interface were between the substrate and the output medium. In these cases, a constituent material of the short-pass filter 247c' is chosen such that each of (i) the mismatch of refractive index $|n_I - n_{SPF}|$ for the sample modified light 135 across an input optical interface between the short-pass filter 247c' and the input medium upstream from the monolithic band-limited ICE 240c and (ii) a mismatch of refractive index $|n_{SPF} - n_{LN}|$ for the filtered light across an optical interface between the short-pass filter 247c' and the last layer $L_N$ of the ICE core 245 is smaller than the mismatch of refractive index $|n_I - n_{LN}|$ for the sample modified light 135 if the input optical interface were between the input medium and the last layer $L_N$ of the ICE core 245.

In alternative cases, when the short-pass filter 247c' is integrally-formed on the substrate and the long-pass filter 247c is integrally-formed on the last layer $L_N$ of the stacked dielectric layers of the ICE core 245 (not shown in FIG. 2B), a constituent material of the short-pass filter 247c' is chosen such that each of (i) the mismatch of refractive index $|n_S - n_{SPF}|$ for the processed light 155 across the optical interface between the substrate and the short-pass filter 247c and (ii) a mismatch of refractive index $|n_{SPF} - n_O|$ for the processed light 155 across an output optical interface between the short-pass filter 247c' and the output medium downstream from the monolithic band-limited ICE 240c is smaller than the mismatch of refractive index $|n_S - n_O|$ for the processed light 155 if the output optical interface were between the substrate and the output medium. In these cases, a constituent material of the long-pass filter 247c is chosen such that each of (i) the mismatch of refractive index $|n_I - n_{LPF}|$ for the sample modified light 135 across an input optical interface between the long-pass filter 247c and the input medium upstream from the monolithic band-limited ICE 240c and (ii) a mismatch of refractive index $|n_{LPF} - n_{LN}|$ for the filtered light across an optical interface between the long-pass filter 247c and the last layer $L_N$ of the ICE core 245 is smaller than the mismatch of refractive index $|n_I - n_{LN}|$ for the sample modified light 135 if the input optical interface were between the input medium and the last layer $L_N$ of the ICE core 245.

Figure 3:
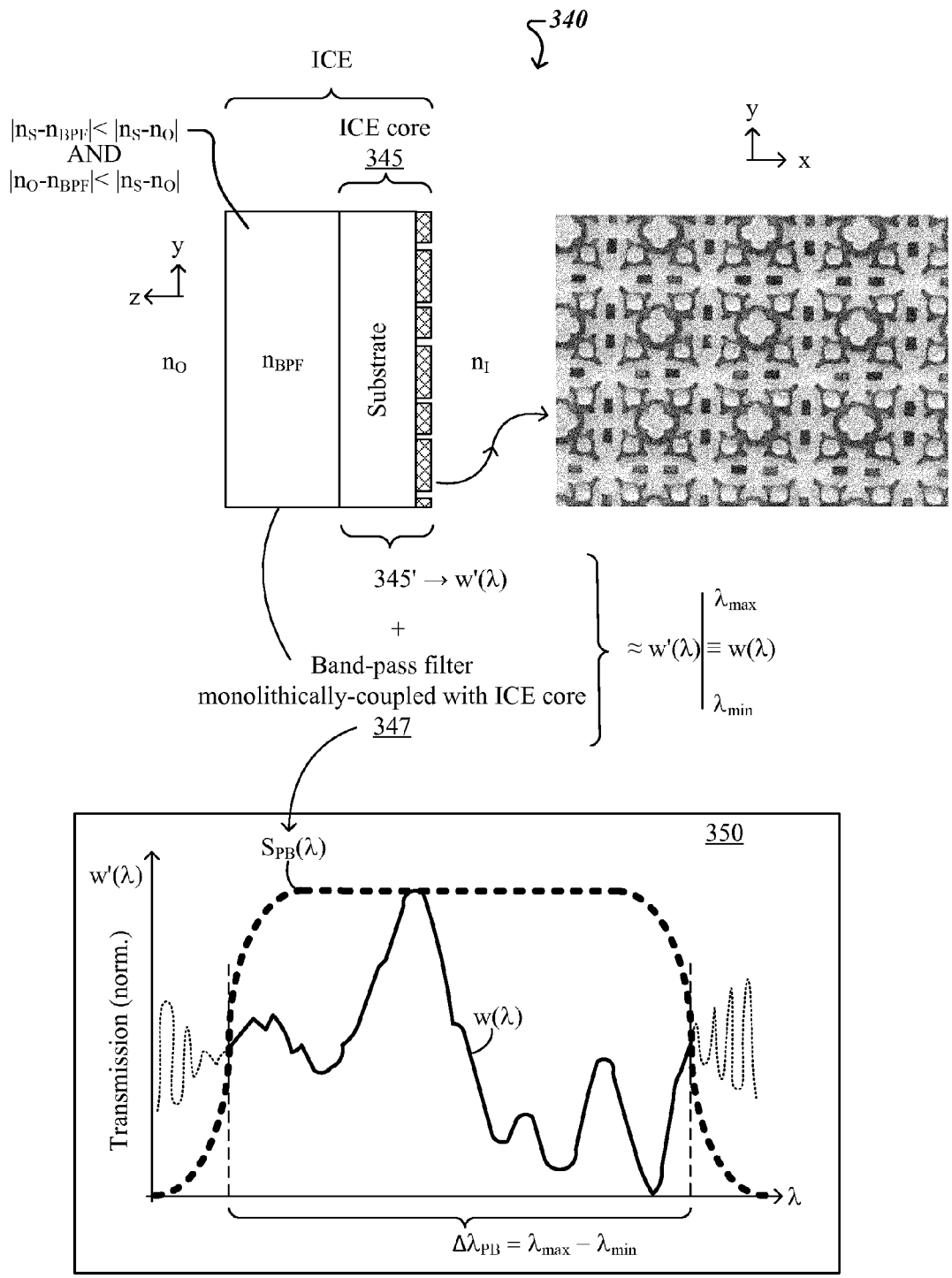
FIG. 3 shows an example of a monolithic band-limited ICE with an ICE core that includes a frequency selective surface.

FIG. 3 shows an example of a monolithic band-limited ICE 340 with an ICE core 345 that includes a frequency selective surface. Here, the monolithic band-limited ICE 340 further includes a band-pass filter 347 that is monolithically coupled to the ICE core 345. The monolithic band-limited ICE 340 represents another embodiment of the monolithic band-limited ICE 140 of the optical analysis tool 110 described above in connection with FIG. 1.

In this example, the ICE core 345 includes a layer of conductive material (hashed-filled in FIG. 3) patterned as laterally-displaced periodic structures over a dielectric substrate, such that the patterned layer forms a frequency-selective surface (FSS). A set of ICE core design parameters 345' of the ICE core 345—which here includes one or more of dimensions of lateral features of the FSS pattern, materials and thicknesses of the substrate and patterned layer, and one or more arrangements of the lateral features of the FSS pattern, e.g., triangular, rectangular, hexagonal or circular—corresponds to an optical spectrum $w'(\lambda)$ associated with the ICE core 345.

For example, the substrate material can be diamond, Ge, ZnSe (or other transparent dielectric material over the wavelength range $[\lambda_{min},\lambda_{max}]$), and can have a thickness in the range of 0.02-2 mm, for instance, to insure structural integrity of the ICE core 345. Materials of the conductive layer reflect the sample modified light 135. A thickness of the conductive layer is typically at least three skin depths. The skin depth depends on the materials (Al, Au, Ag, etc.) of the conductive layer and on the wavelength of the sample modified light 135. In this manner, the thickness of the conductive layer for the ICE core 345 can be in the range of 0.05 to 2 µm, for instance. The optical properties (reflectivity, transmissivity, absorptivity, polarization dependence, angular dependence, etc.) of the FSS of the ICE core 345 are primarily dependent on the physical shape and dimensions of the periodic array of conductive patches or array of apertures in the conductive layer and the refractive index $n_S$ of the substrate upon which the conductive layer is patterned. The pattern of the conductive layer making up the FSS can be quite complicated, often blurring the distinction between arrays of "pure" conductive patches and arrays of "pure" apertures in the conductive layer. In the (x,y)-view of the FSS example shown in FIG. 3, holes or apertures were formed in periodic conductive patches, and isolated conductive islands or patches were disposed in periodic array of holes formed in the conductive layer.

The set of ICE core design parameters 345' is chosen such that the optical spectrum $w'(\lambda)$ associated with the ICE core 345 is spectrally equivalent, over the wavelength range $[\lambda_{min},\lambda_{max}]$, to an optical spectrum $w(\lambda)$ 350 associated with a characteristic of a sample to be measured. Contributions of the optical spectrum $w'(\lambda)$ associated with the ICE core 345 that are from wavelengths outside the wavelength range $[\lambda_{min},\lambda_{max}]$ are removed from the processed light by the band-pass filter 347 monolithically coupled to the ICE core 345, to reduce analysis noise potentially caused by such "outside-of-band" contributions which may not be spectrally equivalent to the optical spectrum $w(\lambda)$ 350 associated with the characteristic to be measured.

In some implementations, the band-pass filter 347 is integrally formed on a surface of the substrate of the ICE core 345 opposing a surface of the substrate on which the conductive layer is patterned to generate the FSS. In other implementations, the conductive layer of the ICE core 345 can be patterned to generate the FSS on a substrate that includes (is pre-formed with) the band-pass filter 347, for instance. In either of these implementations, the band-pass filter 347 can be formed from one or more constitutive materials. For example, the constitutive materials of the band-pass filter 347 can be mixed in a matrix. In this case, an effective refractive index $n_{BPF}$ associated with the band-limiting filter 347 is a weighted average of individual refractive indices of the constitutive materials. As another example, the constitutive materials of the band-pass filter 347 can be formed as a stack of layers, e.g., as an interference filter. In this case, the effective refractive index $n_{BPF}$ associated with the band-limiting filter 347 is a particular function of individual refractive indices of the constitutive layer materials as described in literature, e.g., for ADI filters.

A pass-band envelope $S_{PB}(\lambda)$ of the band-pass filter 347 (represented in the graph of FIG. 3 as a dashed-curve) is overlaid on the optical spectrum $w'(\lambda)$ associated with the ICE core 345. A pass-band $\Delta\lambda_{PB}=\lambda_{max}-\lambda_{min}$ of the band-pass filter 347 is chosen to coincide with a portion (represented as a solid curve) of the optical spectrum $w'(\lambda)$ associated with the ICE core 345 that is spectrally equivalent to the optical spectrum $w(\lambda)$ 350 associated with the characteristic to be measured. In this manner, portions (represented as dotted curves) outside of the wavelength range $[\lambda_{min},\lambda_{max}]$ of the optical spectrum $w'(\lambda)$ associated with the ICE core 345 are blocked by the integrally-formed band-pass filter 347.

In some cases, a constituent material of the band-pass filter 347 is chosen such that each of (i) the mismatch of refractive index $|n_S-n_{BPF}|$ for the processed light 155 across the optical interface between the substrate and the band-pass filter 347 and (ii) a mismatch of refractive index $|n_{BPF}-n_O|$ for the processed light 155 across an output optical interface between the band-pass filter 347 and the output medium downstream from the monolithic band-limited ICE 340 is smaller than the mismatch of refractive index $|n_S-n_O|$ for the processed light 155 if the output optical interface were between the substrate and the output medium.

Figure 4:
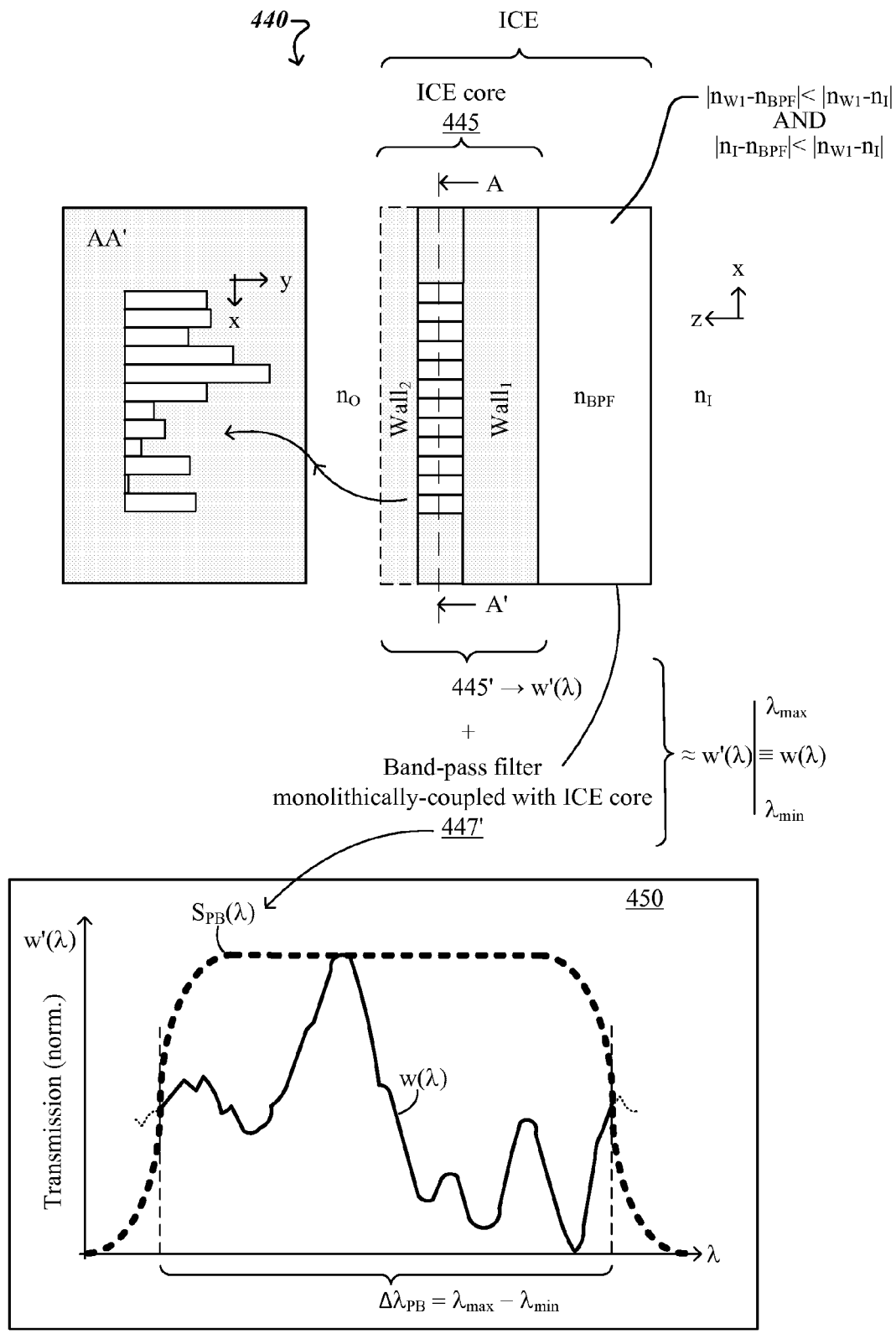
FIG. 4 shows an example of a monolithic band-limited ICE with an ICE core that includes laterally-distributed spectral filters.

FIG. 4 shows an example of a monolithic band-limited ICE 440 with an ICE core 445 that includes laterally-distributed spectral filters. Here, the monolithic band-limited ICE 440 further includes a band-pass filter 447' that is monolithically coupled to the ICE core 445. The monolithic band-limited ICE 440 represents yet another embodiment of the monolithic band-limited ICE 140 of the optical analysis tool 110 described above in connection with FIG. 1.

In this example, the ICE core 445 includes N spectral filters that are supported by a substrate and laterally-distributed (e.g., in an AA' cross-section of the x-y plane) relative to an input optical interface of the ICE core 445. A set of ICE core design parameters 445' of the ICE core 445—which here includes the total number N of the spectral filters and their relative areas—corresponds to an optical spectrum $w'(\lambda)$ associated with the ICE core 445.

The substrate can be formed from a material that has refractive index $n_S$. The substrate material is non-transparent to the wavelengths within the wavelength range $[\lambda_{min},\lambda_{max}]$ for a transmissive configuration of the ICE core 445 (as shown in FIG. 4.) Alternatively, the substrate material is non-reflective to the wavelengths within the wavelength range $[\lambda_{min},\lambda_{max}]$ for a reflective configuration of the ICE core 445 (not shown in FIG. 4.) Various photosensitive materials can be used as substrates, e.g., color film for measurements in the UV-visible spectral range, or IR-sensitive film for measurements in the IR spectral range. In some implementations, the spectral filters can be distributed over a surface of the substrate. Here, the substrate includes wall$_1$ but not wall$_2$, such that the spectral filters are exposed to the ambient of the ICE core 445. In other implementations, the spectral filters can be distributed within the bulk of the substrate. Here, the substrate includes both wall$_1$ and wall$_2$, such that the spectral filters are contained within the substrate without being exposed to the ambient of the ICE core 445. In either case, relative areas (e.g., in the AA' cross-section of the x-y plane) of the spectral filters are chosen to selectively pass or block (e.g., reflect or absorb) predetermined fractions (e.g., corresponding to the relative lateral area of each filter) of light of different wavelengths. Additionally, the spectral filters can have various lateral dimensions and/or shapes (e.g., aspect ratios.) For example, the spectral filters can be shaped as rectangles (of length "l" and width "d" in the x-y plane), annuluses (like a doughnut), annulus segments (like portions of a doughnut), circle sectors (like a slice of pie), and the like. A lower bound for the lateral dimensions of the spectral filters can be in the range of 2-20 μm, depending on the resolution of (i) a manufacturing system used to generate the spectral filters, and/or (ii) the substrate material.

The set of ICE core design parameters 445' is chosen such that the optical spectrum w'(λ) associated with the ICE core 445 is spectrally equivalent, over the wavelength range [$\lambda_{min}, \lambda_{max}$], to an optical spectrum w(λ) 450 associated with a characteristic of a sample to be measured. Contributions of the optical spectrum w'(λ) associated with the ICE core 445 that are from wavelengths outside the wavelength range [$\lambda_{min}, \lambda_{max}$] are removed from the sample modified light 135 by the band-pass filter 447' monolithically coupled to the ICE core 445, to reduce analysis noise potentially caused by such "outside-of-band" contributions which may not be spectrally equivalent to the optical spectrum w(λ) 450 associated with the characteristic to be measured.

In some implementations, the band-pass filter 447' is integrally formed on a surface of the substrate of the ICE core 445 that supports/protects the spectral filters from the ambient of the ICE core 445. In other implementations, the spectral filters of the ICE core 445 can be supported/protected by a substrate that includes (is pre-formed with) the band-pass filter 447', for instance. In either of these implementations, the band-pass filter 447' can be formed from one or more constitutive materials. For example, the constitutive materials of the band-pass filter 447' can be mixed in a matrix. In this case, an effective refractive index $n_{BPF}$ associated with the band-limiting filter 447' is a weighted average of individual refractive indices of the constitutive materials. As another example, the constitutive materials of the band-pass filter 447' can be formed as a stack of layers, e.g., as an interference filter. In this case, the effective refractive index $n_{BPF}$ associated with the band-limiting filter 447' is a particular function of individual refractive indices of the constitutive layer materials as described in literature, e.g., for ADI filters.

A pass-band envelope $S_{PB}(\lambda)$ of the band-pass filter 447' (represented in the graph of FIG. 4 as a dashed-curve) is overlaid on the optical spectrum w'(λ) associated with the ICE core 445. A pass-band $\Delta\lambda_{PB}=\lambda_{max}-\lambda_{min}$ of the band-pass filter 447' is chosen to coincide with a portion (represented as a solid curve) of the optical spectrum w'(λ) associated with the ICE core 445 that is spectrally equivalent to the optical spectrum w(λ) 450 associated with the characteristic to be measured. In this manner, portions (represented as dotted curves) outside of the wavelength range [$\lambda_{min}, \lambda_{max}$] of the optical spectrum w'(λ) associated with the ICE core 445 are blocked by the integrally-formed band-pass filter 447'.

In some cases, a constituent material of the band-pass filter 447' is chosen such that each of (i) the mismatch of refractive index $|n_I-n_{BPF}|$ for the sample modified light 135 across an input optical interface between an input medium (upstream from the monolithic band-limited ICE 440) and the band-pass filter 447' and (ii) a mismatch of refractive index $|n_{BPF}-n_S|$ for the filtered light across the optical interface between the band-pass filter 447' and the substrate of the ICE core 445 is smaller than the mismatch of refractive index $|n_I-n_S|$ for the sample modified light 135 if the input optical interface were between the input medium and the substrate.

Figure 5C:
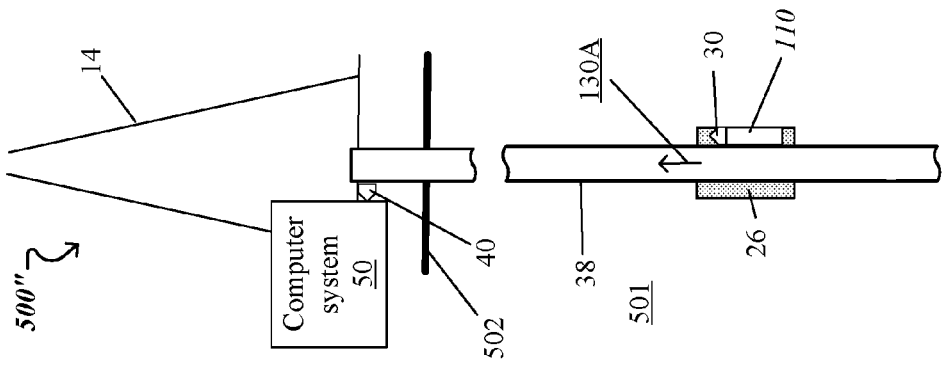
FIGS. 5A-5C show multiple configurations of an example of a system for analyzing wellbore fluids that uses an optical analysis tool including a monolithic band-limited ICE.
Figure 5B:
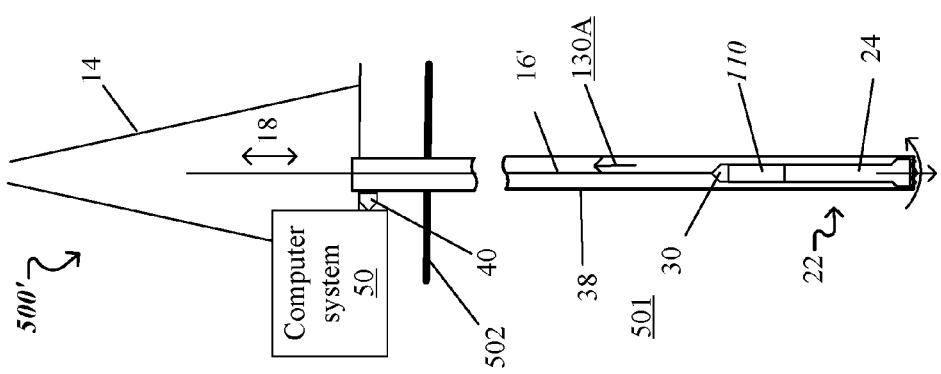
Figure 5A:
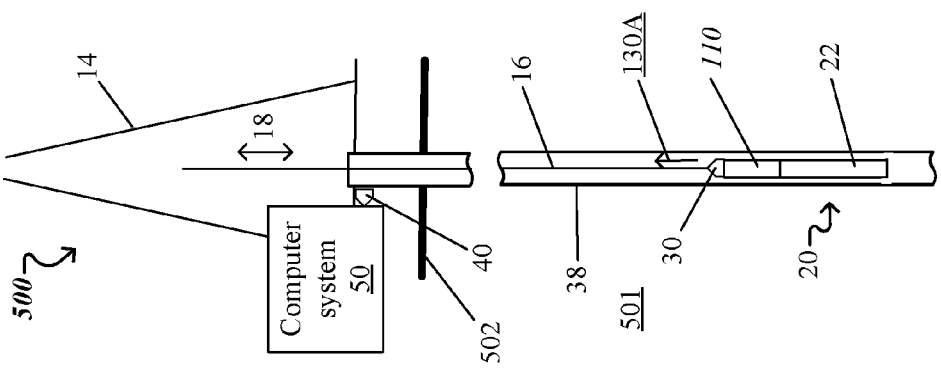

FIGS. 5A-5C show multiple configurations 500, 500', 500" of an example of a system for analyzing wellbore fluids 130A, such that analyses are generated from at least some measurements taken with an optical analysis tool 110, which includes a monolithic band-limited ICE, as the one described above in connection with FIG. 1. Here, the optical analysis tool 110 may be used as a well logging tool, and the disclosed system is referred to as a well logging system.

Each of the configurations 500, 500', 500" of the well logging system illustrated in FIGS. 5A-5C includes a rig 14 above the ground surface 502 and a wellbore 38 below the ground surface. The wellbore 38 extends from the ground surface into the earth 501 and generally passes through multiple geologic formations. In general, the wellbore 38 can contain wellbore fluids 130A. The wellbore fluids 130A can be crude petroleum, mud, water or other substances and combinations thereof. Moreover, the wellbore fluids 130A may be at rest, or may flow toward the ground surface 502, for instance. Additionally, surface applications of the optical analysis tool 110 may include water monitoring and gas and crude transportation and processing.

FIG. 5A shows a configuration 500 of the well logging system which includes a tool string 20 attached to a cable 16 that can be lowered or raised in the wellbore 38 by draw works 18. The tool string 20 includes measurement and/or logging tools to generate and log information about the wellbore fluids 130A in the wellbore 38. In the configuration 500 of the well logging system, this information can be generated as a function of a distance (e.g., a depth) with respect to the ground surface 502. In the example illustrated in FIG. 5A, the tool string 20 includes the optical analysis tool 110 configured as a well logging tool, one or more additional well logging tool(s) 22, and a telemetry transmitter 30. Each of the optical analysis tool 110 and the well logging tool(s) 22 measures one or more characteristics of the wellbore fluids 130A. In some implementations, the optical analysis tool 110 determines values of the one or more characteristics in real time and reports those values instantaneously as they occur in the flowing stream of wellbore fluids 130A, sequentially to or simultaneously with other measurement/logging tools 22 of the tool string 20.

FIG. 5B shows another configuration 500' of the well logging system which includes a drilling tool 24 attached to a drill string 16'. The drilling tool 24 includes a drill bit 26, the ICE-based optical analysis tool 110 configured as a measurement while drilling (MWD) and/or logging while drilling (LWD) tool, and the telemetry transmitter 30. Drilling mud is provided through the drill string 16' to be injected into the wellbore 38 through ports of the drill bit 26. The injected drilling mud flows up the wellbore 38 to be returned above the ground level 502, where the returned drilling mud can be resupplied to the drill string 16' (not shown in FIG.

5B). In this case, the MWD/LWD-configured optical analysis tool 110 generates and logs information about the wellbore fluids 130A (e.g., drilling mud in this case) adjacent the working drill bit 26.

FIG. 5C shows yet another configuration 500" of the well logging system which includes a permanent installation adjacent to the wellbore 38. In some implementations, the permanent installation is a set of casing collars that reinforce the wellbore 38. In this case, a casing collar 28 from among the set of casing collars supports the optical analysis tool 110 configured as a well logging tool and the telemetry transmitter 30. In this manner, the optical analysis tool 110 determines and logs characteristics of the wellbore fluids 130A adjacent the underground location of the casing collar 28.

In each of the above configurations 500, 500' and 500" of the system, the values of the one or more characteristics measured by the optical analysis tool 110 are provided (e.g., as a detector signal 165) to the telemetry transmitter 30. The latter communicates the measured values to a telemetry receiver 40 located above the ground surface 502. The telemetry transmitter 30 and the telemetry receiver 40 can communicate through a wired or wireless telemetry channel. In some implementations of the system configurations 500, 500' illustrated in FIGS. 5A and 5B, e.g., in slickline or coiled tubing applications, measurement data generated by the optical analysis tool 110 can be written locally to memory of the optical analysis tool 110.

The measured values of the one or more characteristics of the wellbore fluids 130A received by the telemetry receiver 40 can be logged and analyzed by a computer system 50 associated with the rig 14. In this manner, the measurement values provided by the optical analysis tool 110 can be used to generate physical and chemical information about the wellbore fluids 130A in the wellbore 38.

Characteristics of the wellbore fluids 130 that can be related to the modified spectrum 135' through the optical spectra associated with the ICE core 145 and other ICE cores (not shown in FIG. 1) of the monolithic band-limited ICE 140 are concentrations of one of asphaltene, saturates, resins, aromatics; solid particulate content; hydrocarbon composition and content; gas composition C1-C6 and content: $CO_2$, $H_2S$ and correlated PVT properties including GOR, bubble point, density; a petroleum formation factor; viscosity; a gas component of a gas phase of the petroleum; total stream percentage of water, gas, oil, solid articles, solid types; oil finger printing; reservoir continuity; oil type; and water elements including ion composition and content, anions, cations, salinity, organics, pH, mixing ratios, tracer components, contamination, or other hydrocarbon, gas, solids or water property.

Some embodiments have been described in detail above, and various modifications are possible. While this specification contains many specifics, these should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Other embodiments fall within the scope of the following claims.

What is claimed is:

1. An optical analysis tool comprising:
   an integrated computational element (ICE) comprising
      an ICE core to process light received by the ICE from a sample, when the tool is operated, such that the processed light is related, over a wavelength range, to a characteristic of the sample, and
      a filter monolithically coupled to the ICE core, the filter to block light at wavelengths that are either shorter than the wavelength range or longer than the wavelength range, or both, such that the ICE outputs, when the tool is operated, the processed light that is passed by the filter,
      wherein each of (i) a mismatch of refractive index for the processed light across an optical interface between the ICE core and the filter and (ii) a mismatch of refractive index for the processed light across an output optical interface between the filter and an output medium downstream from the ICE is smaller than a mismatch of refractive index for the processed light if the output optical interface is between the ICE core and the output medium.

2. The optical analysis tool of claim 1, wherein the filter is a band-pass filter to block the light at the wavelengths that are shorter and longer than the wavelength range, such that the ICE outputs, when the tool is operated, the processed light within the wavelength range.

3. The optical analysis tool of claim 1, wherein
   the filter is a long-pass filter to block the light at the wavelengths that are shorter than the wavelength range, and
   the ICE further comprises a short-pass filter monolithically coupled to the ICE core, the short-pass filter to block light at the wavelengths that are longer than the wavelength range, such that the ICE outputs, when the tool is operated, the processed light within the wavelength range.

4. The optical analysis tool of claim 3, wherein each of (i) a mismatch of refractive index for the received light across an input optical interface between the short-pass filter and an input medium upstream from the ICE and (ii) a mismatch of refractive index for the short-pass filtered light across an optical interface between the ICE core and the short-pass filter is smaller than a mismatch of refractive index for the received light if the input optical interface were between the ICE core and the input medium.

5. The optical analysis tool of claim 1, further comprising:
   a light source positioned to illuminate the sample with light having a first spectrum over the wavelength range, wherein the ICE is positioned to receive the light provided by the sample in response to the illumination, such that the light received from the sample has a second spectrum over the wavelength range, the second spectrum corresponding to the first spectrum modified by the sample; and
   an optical transducer positioned to receive the processed light from the ICE and produce a signal having a value related to an integrated intensity of the processed light across the wavelength range, wherein the signal value corresponds to a value of the characteristic of the sample.

6. The optical analysis tool of claim 5, wherein the optical transducer is spaced apart from the ICE, such that the output medium downstream from the ICE is ambient between the ICE and the optical transducer.

7. The optical analysis tool of claim 5, wherein the optical transducer is monolithically coupled to the filter of the ICE, such that the output medium downstream from the ICE is a constituent material of the optical transducer.

8. The optical analysis tool of claim 5, wherein the ICE is spaced apart from the sample, such that the input medium upstream from the ICE is ambient between the sample and the ICE.

9. The optical analysis tool of claim 5, wherein the short-pass filter of the ICE is adjacent the sample, such that the input medium upstream from the ICE is a constituent material of the sample.

10. The optical analysis tool of claim 1, wherein the ICE core comprises
a substrate having a first surface and a second surface, wherein the substrate comprises a substrate material with a substrate material refractive index, and
a layer of material patterned on the first surface of the substrate such that the processed light is related, over the wavelength range, to the characteristic of the sample, the layer of patterned material comprising a plurality of identical features arranged in an array, and the features each comprising one or more geometric shapes selected from the group consisting of triangles, quadrilaterals, hexagons, and circles.

11. The optical analysis tool of claim 10, wherein constituent material of the filter is stacked on the second surface of the substrate.

12. The optical analysis tool of claim 10, wherein constituent material of the filter is included within the substrate between the first and second surfaces thereof.

13. The optical analysis tool of claim 1, wherein the ICE core comprises
a substrate having a first surface and a second surface, wherein the substrate comprises a substrate material with a substrate material refractive index, and
a plurality of spectral filters supported by the substrate adjacent to the first surface and arranged at different lateral positions with respect to a path of the light received from the sample, each spectral filter formed to transmit or reflect a different subset of wavelengths in the wavelength range, and each spectral filter having a respective area exposed to the light from the sample, the respective areas being related to a property of the sample.

14. The optical analysis tool of claim 13, wherein constituent material of the filter is stacked on the second surface of the substrate.

15. The optical analysis tool of claim 13, wherein a constituent material of the filter is included within the substrate between the first and second surfaces thereof.

16. The optical analysis tool of claim 1, wherein the wavelength range comprises wavelengths in a range from about 0.2 μm to about 25 μm.

17. An optical analysis tool comprising:
an integrated computational element (ICE) comprising
an ICE core to process light received by the ICE from a sample, when the tool is operated, such that the processed light is related, over a wavelength range, to a characteristic of the sample,
a long-pass filter monolithically coupled to the ICE core, the filter is a long-pass filter to block light at wavelengths that are shorter than the wavelength range, wherein a value of an effective refractive index $n_F$ associated with the long-pass filter is bound by a value of an effective refractive index associated with the ICE core and a value of a refractive index of an output medium downstream from the ICE, and
a short-pass filter monolithically coupled to the ICE core, the short-pass filter to block light at the wavelengths that are longer than the wavelength range, such that the ICE outputs, when the tool is operated, processed light within the wavelength range, wherein a value of an effective refractive index associated with the short-pass filter is bound by a value of the effective refractive index associated with the ICE core and a value of a refractive index of an input medium upstream from the ICE.

18. The optical analysis tool of claim 17, wherein the wavelength range comprises wavelengths in a range from about 0.2 μm to about 2.5 μm.

19. The optical analysis tool of claim 17, wherein the wavelength range comprises wavelengths in a range from about 2.5 μm to about 25 μm.

20. A well logging system comprising:
an optical analysis tool that comprises
an integrated computational element (ICE) comprising
an ICE core to process light received by the ICE from a sample, when the tool is operated, such that the processed light is related, over a wavelength range, to a characteristic of the sample, wherein the ICE core comprises
a substrate having a first surface and a second surface, wherein the substrate comprises a substrate material with a substrate material refractive index, and
a plurality of layers stacked on the first surface of the substrate, wherein adjacent ones of the plurality of layers respectively comprise layer materials with refractive indices different from each other, wherein a substrate thickness and thicknesses of the plurality of layers are such that the processed light is related, over the wavelength range, to the characteristic of the sample, and
a filter monolithically coupled to the ICE core, the filter to block light at wavelengths that are either shorter than the wavelength range or longer than the wavelength range, or both, such that the ICE outputs, when the tool is operated, the processed light that is passed by the filter, wherein constituent material of the filter is stacked on the second surface of the substrate,
wherein each of (i) a mismatch of refractive index for the processed light across an optical interface between the substrate and the constituent material of the filter and (ii) a mismatch of refractive index for the processed light across an output optical interface between the constituent material of the filter and an output medium downstream from the ICE is smaller than the mismatch of refractive index for the processed light if the output optical interface were between the substrate and the output medium; and
wherein the sample comprises wellbore fluids and the characteristic of the sample is a characteristic of the wellbore fluids.

21. The optical analysis tool of claim 20, wherein constituent material of the filter is included within the substrate between the first and second surfaces thereof.

22. The optical analysis tool of claim 20, wherein
the filter is a long-pass filter to block the light at the wavelengths that are shorter than the wavelength range, the ICE further comprises a short-pass filter to block light at the wavelengths that are longer than the wavelength range, such that the ICE outputs, when the tool is operated, processed light within the wavelength range, and constituent material of the short-pass filter is stacked on a distal-most surface of the stacked layers relative to the substrate.

23. The optical analysis tool of claim 22, wherein each of (i) a mismatch of refractive index for the received light across an input optical interface between the short-pass filter and an input medium upstream from the ICE and (ii) a mismatch of refractive index for the short-pass filtered light across an optical interface between a distal-most layer of the ICE core relative to the substrate and the short-pass filter is smaller than a mismatch of refractive index for the received light if the input optical interface were between the distal-most layer of the ICE core and the input medium.

24. The well logging system of claim 20, wherein the characteristic of the sample is selected from the group consisting of a concentration of a substance in the sample, a pH of the sample, a ratio of concentrations of two different substances in the sample, a phase of the sample, a density of the sample, and a viscosity of the sample.

* * * * *